United States Patent [19]

Johansson

[11] Patent Number: 4,784,852

[45] Date of Patent: Nov. 15, 1988

[54] COMPOSITION FOR HUMAN SUPPLY OF SELENIUM AS TRACE ELEMENT

[76] Inventor: Erland Johansson, S-752 47, Uppsala, Sweden

[21] Appl. No.: 930,077

[22] Filed: Nov. 12, 1986

Related U.S. Application Data

[63] Continuation of Ser. No. 715,038, Mar. 21, 1985, abandoned, which is a continuation of Ser. No. 509,436, filed as PCT SE82/00304 on Sep. 30, 1982, published as WO83/01196 on Apr. 14, 1983, abandoned.

[30] Foreign Application Priority Data

Oct. 6, 1981 [SE] Sweden .................. 8158877

[51] Int. Cl.$^4$ ............................................. A61K 33/04
[52] U.S. Cl. ...................................... 424/164; 514/905
[58] Field of Search ........................ 424/162, 164, 235

[56] References Cited

U.S. PATENT DOCUMENTS 3,928,578 12/1975 Burns et al. .................... 424/284

FOREIGN PATENT DOCUMENTS 2811222 9/1979 Fed. Rep. of Germany.
2100669 3/1972 France.
1444024 7/1976 United Kingdom.

OTHER PUBLICATIONS

Fed. of Am. Soc. Exp. Biol. -Fed. Procedings, 24 (1) (Part I), Jan.-Feb. 1965, pp 58-64-Schwary, Chem. Abst. 85, 1947, (f) (1976)-Berenshtein.

Primary Examiner—Douglas W. Robinson
Attorney, Agent, or Firm—Harness, Dickey & Pierce

[57] ABSTRACT

A composition for human supply of selenium as a trace element and comprising a selenium (IV) compound or seleno-methionine+a selenium (IV) compound. The admixture into the composition of vitamins E, $B_2$, $B_6$ and $B_{12}$ allows the body to assimilate selenium. The composition may also be used in solutions for storage of organs, in media for cell cultivation and in nutritive solutions for storage of blood components.

7 Claims, No Drawings

COMPOSITION FOR HUMAN SUPPLY OF SELENIUM AS TRACE ELEMENT

This is a continuation of U.S. patent application Ser. No. 715,038, filed Mar. 21, 1985, now abandoned, which is a continuation of Ser. No. 509,436, filed as PCT SE82/00304 on Sep. 30, 1982, published as WO83/01196 on Apr. 14, 1983, now abandoned.

BACKGROUND OF THE INVENTION

The invention concerns a composition designed to supply the trace element selenium into human beings.

In later years, increasing interest has been drawn to the substances known as trace elements, i.e. elements which are absolutely vital to the human organism, albeit in minute amounts. There are clear indications that many diseases and states of ill-health are a consequence of deficiencies of one or several of such trace elements. For example, there are reasons to suspect that certain heavy metals, such as cadmium, which are dissolved upon their contact with acid, such as through acid rains, cause a rise of the blood pressure. Animal tests have shown that cadmium-induced high blood-pressure conditions may be normalized by selenium compounds. Ingestion of the heavy metal cadmium in animals are inducive to damages to the endothelium. This, jointly with an increased blood-pressure and changes in the cholesterol pattern in the blood are considered the primary factors of arteriosclerosis. According to an American study, individuals having a high blood-pressure showed cadmium contents in erythrocytes which were double those found in a control group. Expositions in industry to heavy metals together with an excess ingestion of cadmiun present in food in combination with a selenium-depleted diet may play important parts in the pathogenesis in this regard.

Animal tests (on rats) have shown that iron (aluminium) may trigger off epileptic attacks. When selenium (IV) was ingested with drinking water, no such attacks were triggered off. Patients suffering from epilepsy proved to have low selenium contents in urine. The iron contents in plasma in one patient was considerably increased while the selenium contents were somewhat below the reference amounts. Since high iron contents are considered to start off lipid peroxidation, supplementation of selenium should reduce this disorder.

In cases of prolonged total parenteral nutrition (TPN) food diets having low contents of selenium have proved to cause muscular pain. Ingestion of selenium under certain conditions as will be explained in closer detail in the following, removed these pains completely.

Test have also shown that such muscular diseases as muscular dystrophy, non-specified muscular pains and myositis in many cases are selenium responsive. Also in some multiple-sclerosis patients remarkable improvements from selenium therapy (auto-therapy) have been found.

Additionally, attempts to alleviate rheumatoid arthritis by selenium supplementation has given interesting results. Patients suffering from this disease have increased contents of copper in serum whereas the selenium contents are reduced. In selenium therapy (for instance using Mixture 3) care should be taken to ensure that the treatment continues over a prolonged period, allowing saturation of any metallic ion surplus. Copper has an inhibitory effect on the selenium enzyme (GSH-Px), which means that in an initial stage the activity may increase only slowly.

Finland like Sweden is a selenium-deficit area. The death rate in cardio-vascular diseases in Finland is one of the highest in the world. Exposition to heavy metals, such as cadmium (smoking, food), dietary habits can in these cases reduce the contents of selenium in the thrombocytes. Cardio-vascular patients show lower GSH-Px-values in the thrombocytes. This could be expected, in view of the fact that the thrombocytes are the species in the human body that are the richest in selenium. The hypothesis that also myocardial infarction is selenium-deficiency induced lies near at hand.

One of the reasons for selenium deficiency probably is the increased acidification of the environment, which causes leaching of the food that normally supplies the body with selenium in edible form, for instance in the form of Se(IV) or seleno-methionine. As mentioned above, acidification causes leaching but some investigations indicate that selenium absorption is reduced also as a consequence of "sulfur competition".

Uraemia patients show changed trace element contents in blood, depending on impaired kidney function but also on contamination from e.g. utensils (cadmium, aluminium) in haemodialysis therapy. An excess mortality rate in coronary-vascular diseases is found in this category of patients. Supplementation of trace elements prior to or after dialysis should reduce the mineral imbalance in the body of uraemia patients.

Epidemiological studies have shown that selenium-deficit areas are oppositely correlated to some forms of cancer, such as cancer of the breast, stomach, colon and rectum. Animal tests have shown that selenium compounds ($Na_2SeO_3$, seleno-methionine) have a protective effect against selected mammary-carcinogenic, colon-carcinogenic and liver-carcinogenic compounds. Mutagenic studies of carcinogens likewise show that selenium is effective in reducing significantly the mutagenic activity. It is therefore probable that the diet should contain certain amounts of selenium compounds in order to protect human beings against cancer. The protection could exist at several levels:

(1) protection against nucleotide peroxides;
(2) prevention of imbalance in metal ions;
(3) improvement of the infection and immunity defence;
(4) facilitation of the microsomale detoxification;
(5) anti-oxidant protection against lipid peroxides;
(6) radical modulator.

The daily intake should be higher than that recommended by RDA, which is 50–200 μg Se/day. To obtain a cancer-inhibitory effect it is considered that the intake should be about 200–350 μg Se/day.

Treatment of various cancer forms with anticancer compounds, e.g. adriamycine, has considerable negative effects, such as a high cardiac toxicity. Since selenium compounds ($Na_2SeO_3$, seleno-methionine) have a beneficial effect on some muscular diseases, selenenium supplementation (storing) prior to and during treatment with anticancerous preparations (also in combination with radiology treatment) should be effective in reducing some of the negative effects of anticancer compounds. Considering that the microsomal function is affected by selenium deficiency an increase of the selenium level will contribute additionally to reducing the toxic effect of the carcinocidal substances.

Patients suffering from diabetic cataract have been successfully treated with selenium plus Vitamin E. Animal tests have shown that seleno-methionine is preferable to sodium selenite to treat cataract. Selenium deficiency is assumed to increase the lipid peroxidation and thus result in an increase of pigmentation. Selenium therapy tested on cataract patients in Sweden has given positive results.

SUMMARY OF THE INVENTION

The purpose of the invention is to provide a formula by means of which selenium may be supplied in such a form that the body is capable of absorbing selenium as a trace element. For this purpose the invention concerns a composition for human supply of selenium as a trace element but also for normalizing imbalance in the mineral status of the body.

This composition is characterised in that it contains a selenium (IV) compound or such a compound in combination with seleno-methionine in an amount corresponding to between 50 and 500 µg of selenium, Vitamin E in amounts of between 10 and 100 mg, Vitamin $B_2$ in amounts of between 1 and 5 mg, Vitamin $B_6$ in amounts between 2 and 10 mg and Vitamin $B_{12}$ in amounts between 1 and 5 µg. Owing to the formulation of the composition the body absorbs selenium Se(IV) and seleno-methionine.

As apparent from the dependent claims the composition is to have a certain formulation when intended for pharmaceutical uses. The purpose of the invention is also to prevent selenium deficiency, in which case the composition in accordance with the invention is to be supplied as food supplementation and preferably be formulated as follows:

Formulation I:
  Se(IV) in an amount corresponding to 100 ug selenium,
  Vitamin E in an amount of 10 mg,
  Vitamin $B_2$ in an amount of 1.5 mg,
  Vitamin $B_6$ in an amount of 2.0 mg, and preferably
  Vitamin $B_{12}$ in an amount of 2.0 ug.

Formulation II:
  Se(IV) in an amount corresponding to 100 ug selenium, and
  seleno methionine in an amount corresponding to between 50 and 500 ug selenium,
  Vitamin E in an amount of 10 mg,
  Vitamin $B_2$ in an amount of 1.5 mg,
  Vitamin $B_6$ in an amount of 2.0 mg, and preferably
  Vitamin $B_{12}$ in an amount of 2.0 ug.

The amounts specified in the claims are intended daily doses for adults of normal weight, and some modification of the daily amounts therefore is possible and sometimes also recommendable. The amounts specified therefore are to be regarded as an indication of the mutual relationship between the substances of which the mixture is composed.

DESCRIPTION OF THE INVENTION

Tests have further shown that a composition in accordance with the subject invention also has efficient therapeutic effects in relieving and healing inflammatory conditions, that is, to strengthen the body's natural resistance against inflammations of the skin, the effects of surgical operations, microorganism-induced inflammations, virus attacks, and so on.

Much remains to be understood as regards the exact mechanisms connected with Se(IV) and seleno-methionine, but research carried out to date indicate that selenium is of extremely great importance as a trace element in the body and this research suggests that the importance of selenium extends also to many other functions of the body, among them the enzyme production and the effect of enzymes.

Finally, it should be pointed out that the invention is not limited to only the formulations indicated herein but that obviously the addition thereto of further trace elements is possible, in which case it should be understood that it is necessary to ensure that such added elements are compatible with the rest of the substances making up the composition. For instance, admixture of additives facilitating the metal-ion balance in metal-ion-depending enzymes lies within the scope of the subject invention, examples of such additives being manganese, chromium, magnesium and zinc.

EXAMPLES

The following examples of the composition of tablets are to be regarded as illustrative of the invention and in no way to limit the latter.

Food supplementation

| Example 1 | Sodium selenite ($Na_2SeO_3.5H_2O$) | 50 µg (Se(IV)) |
|---|---|---|
| | Vitamin E (α-tocopheryl acetate) | 10 mg |
| | Vitamin $B_2$ (sodium riboflavine phosphate) | 1.5 mg |
| | Vitamin $B_6$ (pyridoxine chloride) | 2 mg |
| | Vitamin $B_{12}$ (cyancobolamin) | 1 µg |
| | Fillers, such as magnesium stearate | |
| Dosage: | 1 tablet/day. Children, adults | |

| Example 2 | Sodium selenite ($Na_2SeO_3.5H_2O$) | 25 µg Se |
|---|---|---|
| | Seleno-methionine | 25 µg Se |
| | Vitamin E | 10 mg |
| | Vitamin $B_2$ | 1.5 mg |
| | Vitamin $B_6$ | 2 mg |
| | Vitamin $B_{12}$ | 1 µg |
| | Fillers, such as magnesium stearate | |
| Dosage: | 1 tablet/day. Children, adults | |

Therapy

| Example 1 | Sodium selenite ($Na_2SeO_3.5H_2O$) | 200 µg Se |
|---|---|---|
| | Vitamin E (α-tocopheryl acetate) | 100 mg |
| | Vitamin $B_2$ (sodium riboflavine phosphate) | 1.5 mg |
| | Vitamin $B_6$ (pyridoxine chloride) | 2 mg |
| | Vitamin $B_{12}$ (cyancobolamin) | 1 µg |
| | Fillers, such as magnesium stearate | |
| Dosage: | 1 to 2 tablets/day according to need. 500 µg Se/day should not be exceeded unnecessarily in cases of prolonged therapy. | |

Therapy

| Example 2 | Sodium selenite ($Na_2SeO_3.5H_2O$) | 100 µg Se |
|---|---|---|
| | Seleno-methionine | 100 µg Se |
| | Vitamin E | 100 mg |
| | Vitamin $B_2$ | 1.5 mg |
| | Vitamin $B_6$ | 2 mg |
| | Vitamin $B_{12}$ | 1 µg |
| | Fillers, such as magnesium stearate | |
| Dosage: | 1 to 2 tablets/day according to need. 500 µg Se/day should not be exceeded unnecessarily in cases of prolonged therapy. | |

In case of pernicious anameia or leukaemia (leukaemian conditions) Vitamin $B_{12}$ should be removed from the composition and be administered according to need as per special prescription.

The tablets should be taken together with food for optimal effect. Large amounts of juice (Vitamin C) should not be taken together with the tablets. Juice may be taken after the absorption of the tablets.

What I claim is:

1. An improved composition for increasing the bioavailability of selenium as a trace element, said composition containing
   seleno methionine and sodium selenite in amounts corresponding to between 50 and 500 ug selenium,
   Vitamin E in amounts of between 10 and 100 mg,
   Vitamin $B_2$ in amounts of between 1 and 5 mg, and
   Vitamin $B_6$ in amounts of between 2 and 10 mg.

2. An improved composition according to claim 1 for use as food supplementation, said composition containing
   seleno methionine and sodium selenite in an amount corresponding to 100 ug selium,
   Vitamin E in an amount of 10 mg,
   Vitamin $B_2$ in an amount of 1.5 mg,
   Vitamin $B_6$ in an amount of 2 mg, and preferably
   Vitamin $B_{12}$ in an amount of 2 ug.

3. An improved composition according to claim 1 for therapeutical uses, said composition containing
   seleno methionine and sodium selenite in an amount corresponding to 200 ug selium,
   Vitamin E in an amount of 10 mg,
   Vitamin $B_2$ in an amount of 1.5 mg,
   Vitamin $B_6$ is an amount of 2 mg, and preferably
   Vitamin $B_{12}$ in an amount of 2 ug.

4. An improved composition according to claim 1, comprising said composition in a solution compatible with said composition for storage of organs.

5. An improved composition according to claim 1, comprising said composition in a cell-cultivation medium compatible with said composition.

6. An improved composition according to claim 1, comprising said composition in a nutritive solution compatible with said composition for storage of blood components.

7. An improved composition according to claim 1 comprising, in addition, Vitamin $B_{12}$ in amounts of between 1 and 5 $\mu$g.

* * * * *

UNITED STATES PATENT AND TRADEMARK OFFICE
CERTIFICATE OF CORRECTION

PATENT NO. : 4,784,852
DATED : November 15, 1988
INVENTOR(S) : Erland Johansson

It is certified that error appears in the above-identified patent and that said Letters Patent is hereby corrected as shown below:

Foreign Application Priority Data: "8158877" should be --81058877--

Other References: "1947," should be --19471--

Column 1, line 59, "has" should be --have--

Column 2, line 32, "($Na_2SeO_3$)" should be --($Na_2SeO_3$--

Column 3, line 21, "the" should be --this--

Column 5, line 20, "selium" should be --selenium--

Column 6, line 5, "selium" should be --selenium--

Signed and Sealed this

Sixth Day of February, 1990

*Attest:*

JEFFREY M. SAMUELS

*Attesting Officer*   *Acting Commissioner of Patents and Trademarks*